United States Patent [19]

Knutsen et al.

[11] Patent Number: 5,578,582
[45] Date of Patent: Nov. 26, 1996

[54] METHODS OF TREATING ISCHEMIA WITH C2, N6-DISUBSTITUTED ADENOSINE DERIVATIVES

[75] Inventors: Lars J. Knutsen, Vedbæk; Jesper Lau, Farum, both of Denmark

[73] Assignee: Novo Nordisk A/S, Bagsvaerd, Denmark

[21] Appl. No.: 435,005

[22] Filed: May 5, 1995

Related U.S. Application Data

[62] Division of Ser. No. 963,878, filed as PCT/DK91/00324 Oct. 24, 1991, Pat. No. 5,432,164.

[51] Int. Cl.$^6$ .................... A61K 31/70; C07H 19/167
[52] U.S. Cl. ............................. 514/46; 536/27.63
[58] Field of Search ............... 514/46; 536/27.63

[56] References Cited

U.S. PATENT DOCUMENTS

| | | | |
|---|---|---|---|
| 3,796,700 | 3/1974 | Yoshioka et al. | 260/211.5 |
| 5,432,164 | 7/1995 | Knutsen et al. | 514/46 |

FOREIGN PATENT DOCUMENTS

| | | |
|---|---|---|
| 0253962 | 1/1988 | European Pat. Off. |
| 0402752 | 12/1990 | European Pat. Off. |
| 0423777 | 4/1991 | European Pat. Off. |
| 1351501 | 5/1974 | United Kingdom. |

*Primary Examiner*—Douglas W. Robinson
*Assistant Examiner*—Gary L. Kunz
*Attorney, Agent, or Firm*—Steve T. Zelson, Esq.; Elias J. Lambiris, Esq.

[57] ABSTRACT

This application relates to methods of treating myocardial or cerebral ischemia, comprising administering a compound of formula I:

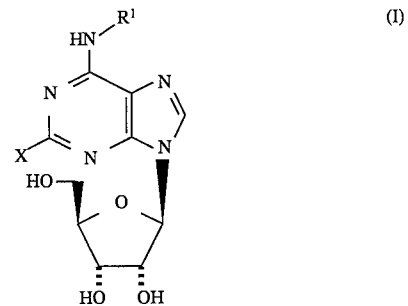

wherein

X is halogen, perhalomethyl, cyano, $C_{1-6}$-alkoxy, $C_{1-6}$-alkylthio or $C_{1-6}$-alkylamino; and $R^1$ is selected from N-bonded heterocycles.

The compound with the greatest ability to discriminate between the A1 and A2 adenosine receptors is 2-chloro-N-[4-phenoxy-1-piperidinyl]adenosine.

16 Claims, No Drawings

METHODS OF TREATING ISCHEMIA WITH C2, N⁶-DISUBSTITUTED ADENOSINE DERIVATIVES

This is a divisional application of application Ser. No. 07/963,878, filed, as PCT/DK91/00324 Oct. 24, 1991, now U.S. Pat. No. 5,432,164 the contents of which are incorporated herein by reference in their entirety.

The present invention relates to modified 6-hydrazino-9-(β-D-ribofuranosyl)-(9H)-purines further substituted at the 2-position and pharmaceutically acceptable addition salts thereof having certain very desirable central nervous system properties, processes for their preparation and their pharmaceutical compositions as well as methods for using the compounds and compositions described.

BACKGROUND OF THE INVENTION

Adenosine can be considered to be a hormone which has been shown to have a number of significant effects on the mammalian central nervous system (CNS) [see, for example, Adenosine in the Nervous System (in the series Neuroscience Perspectives, Series Editor Jenner, P.) Stone, T. W., Ed., Academic Press Ltd., London, 1991, Annual Reports in Medicinal Chemistry, 1988, 23, 39–48; International Review of Neurobiology (Smythies, J. R. and Bradley, R. J., eds.) Academic Press Inc., 1985, 27, 63–139.], especially under conditions of neuronal stress where the compound appears to act as an endogenous neuro-protectant (Progress in Neurobiology, 1988, 31, 85–108, Trends in Pharmacological Sciences, 1988, 9, 193–194). For example, the concentration of adenosine has been demonstrated to rise greatly in certain brain regions following epileptic seizures or conditions of neuronal ischaemia/anoxia, (Brain Research 1990, 516, 248–256).

It has been established for some years now that centrally acting adenosine receptor agonists or compounds which increase extracellular adenosine levels can exhibit what is termed neuromodulator activity. Such substances influence the release of neurotransmitters in regions of the central nervous system (Annual Review of Neuroscience, 1985, 8, 103–124; Trends in Neurosciences, 1984, 164–168), with particular inhibitory effects on the release of the excitatory amino acid glutamic acid (glutamate) (Nature, 1985, 316, 148–150, Journal of Neurochemistry, 1992, 58, 1683–169).

There are several CNS ailments in which this adenosine receptor mediated neuromodulator activity may be of clear therapeutic benefit. Examples of these would include the treatment of convulsive disorders (European Journal of Pharmacology, 1991, 195, 261–265; Journal of Pharmacology and Experimental Therapeutics, 1982, 220, 70–76), prevention of neurodegeneration under conditions of brain anoxia/ischaemia (Neuroscience, 1989, 30, 451–462; Neuroscience Letters, 1987, 83, 287–293; Medical Hypotheses, 1990, 32, 45–49, Pharmacology of Cerebral Ischaemia 1990 (Kriegelstein, J. and Oberpichler, H., Eds., Wissenschaftliche Verlagsgesellschaft mbH: Stuttgart, 1990, pp 439–448) or the use of a purinergic agent in the treatment of pain (European Journal of Pharmacology, 1989, 162, 365–369; Neuroscience Letters, 1991, 121, 267–270). The relevance of adenosine and adenosine agonists to all these disease areas has recently been reviewed in Adenosine and Adenine Nucleotides as Regulators of Cellular Function (Phyllis, J. W., Ed., CRC Press Inc: Boca Raton, Fla., 1991, pp 319–400).

Adenosine receptors represent a subclass ($P_1$) of the group of purine nucleotide and nucleoside receptors known as purinoreceptors. This subclass has been further classified into two distinct receptor types which have become known as A1 and A2. Extensive research has been carried out in a quest to identify selective ligands at these sites [see, for example, Comprehensive Medicinal Chemistry, Volume 3, (Hansch, C., Sammes, P. G. and Taylor, J. B., Pergamon Press PLC, 1990, 601–642)].

Selective ligands exist for A1 and A2 adenosine receptors and the structure-activity relationships of the various reference ligands have been reviewed (Biochemical Pharmacology, 1986, 35, 2467–2481) together with their therapeutic potential (Journal of Medicinal Chemistry, 1992, 35, 407–422). Among the known adenosine receptor agonists most selective for the A1 receptor over the A2 receptor are the examples where the adenine nucleus is substituted with a cycloalkyl group on the amino function, for example N-cyclopentyladenosine and N-cyclohexyladenosine (Journal of Medicinal Chemistry, 1985, 28, 1383–1384) or 2-chloro-N-cyclopentyladenosine (Naunyn-Schmiedeberg's Arch. Pharmacol. 1988, 337, 687–689).

Examples of adenosine derivatives in the chemical literature having a nitrogen bonded directly to the 6-amino substituent are few in number, and are summarized below.

They include N-aminoadenosine, N-[(N-methyl-N-phenyl)amino]adenosine (Journal of Medicinal Chemistry, 1985, 28, 1636–1643); N-(methylamino)adenosine and N-[(N-hydroxy-N-methyl)amino]adenosine (Journal of Medicinal Chemistry, 1968, 11, 521–523); 2-amino-N-aminoadenosine (Chemical and Pharmaceutical Bulletin, 1969, 17, 2373–2376); 2-fluoro-N-aminoadenosine (Journal of Medicinal Chemistry, 1970, 13, 427–430) and 2-fluoro-N-methoxyadenosine (Journal of Medicinal Chemistry, 1971, 13; 816–819). Finally, there is one example containing a cyclic amine, namely 2-amino-N-piperidinyladenosine (Arzneimittel-Forschung, 1970, 20, 1749–1751).

In the above scientific articles, no mention is made of any pharmacological effects of the compounds concerned on the central nervous system.

In U.S. Pat. No. 3,819,613, substituted adenosine analogues with hydrazone derivatives on the 6-amino function are disclosed as hypotensive agents. In GB Patent No. 1,351,501, adenosine and 2-aminoadenosine derivatives having a —NH—$R_2$ group joined to the 6-amino function are disclosed as coronary dilators and platelet aggregation inhibitors. In EP Publication No. 152,944A, a series of 2-, 6- and 8- substituted adenosine derivatives are described having activity as anti-allergy agents. In EP Publication No. 253,962A, adenosine and 2-haloadenosine analogues having an alkyl, cycloalkyl or an aralkyl group attached to the 6-amino function are described with activity as antidementia agents.

In EP Publication No. 402,752A, derivatives of adenosine unsubstituted in the 2-position are described which have a substituted heteroaromatic 1-pyrrolyl moiety attached to the 6-amino group. In PCT Publication No. WO 91/04032, methods of preventing neural tissue damage in neuro-degenerative diseases by increasing extracellular concentrations of adenosine are described. Examples are given of prodrug esters of AICA riboside which are claimed to be centrally acting neuroprotective agents. In PCT Publication No. WO 92/02214, analogues of AICA riboside are described which increase extracellular adenosine levels with beneficial effects claimed in peripheral and CNS ischaemia. In PCT Publication No. WO 90/05526, 2-(alkylalkynyl)adenosine derivatives are described for treatment of ischaemic disease of the heart and brain. In EP Publication No. 0 423

777 A2 a method for treating gastrointestinal motility disorders using N(6) (substituted aminoalkyl) adenosine derivatives is disclosed. EP Publication No. 0 490 818 A1 describes a new use of 2'-O-methyl adenosine derivatives for a range of ailments including neurodegenerative disorders.

The present invention relates to new adenosine analogues having remarkably potent binding in vitro to the adenosine A1 receptor and at the same time showing selectivity for A1 receptor binding in vitro over that of the A2 receptor subtype. In addition, the compounds contained in this invention have a relatively high lipophilicity, especially when compared to adenosine analogues which are not substituted on the 6-amino group or the purine 2-position. This latter property makes these compounds suitable for passage across the blood brain barrier, and supports the suggestion that the compounds may be candidate drugs for the CNS ailments mentioned within this invention.

The possibility that some of the compounds may be substrates for nucleoside-specific active transport systems across the blood barrier is, however, not excluded. These useful properties support the suggestion that the compounds may be candidate drugs for the CNS ailments mentioned above in humans. There are instances where it has been demonstrated that co-administration of a peripherally active adenosine receptor antagonist can lower the expected side effects on the cardiovascular system when an adenosine agonist is used as a neuroprotectant in animal models (Journal of Molecular Neuroscience, 1990, 2, 53–59). This method of lowering side-effects is also applicable during the therapeutic use of the adenosine receptor agonists covered by the present invention.

The novel compounds of the invention are purine derivatives of formula (I), or a pharmaceutically acceptable salt thereof:

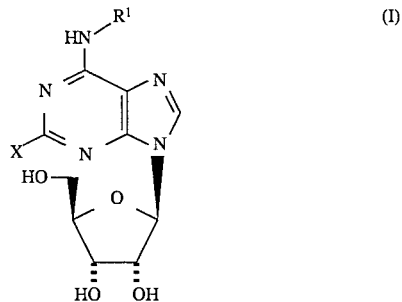
(I)

wherein

X is halogen, perhalomethyl, cyano, $C_{1-6}$-alkoxy, $C_{1-6}$-alkylthio or $C_{1-6}$-alkylamino;

$R^1$ is selected from the groups consisting of

(a)

wherein n is 1 to 3 and where the group (a) may be optionally substituted with one or two $C_{1-6}$-alkyl groups, $C_{2-6}$-alkenyl, $C_{2-6}$-alkynyl, phenoxy, phenylsulphonyl, phenylthio, hydroxy, phenyl, $C_{1-6}$-alkoxy or $C_{1-6}$-alkoxy-$C_{1-6}$-alkyl, phenylthioalkyl or

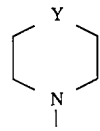
(b)

wherein Y is O, S or NZ, where Z is H, $C_{1-6}$-alkyl or phenyl, and where the group (b) may be optionally substituted with $C_{1-6}$-alkyl, $C_{2-6}$-alkenyl, $C_{2-6}$-alkynyl, phenoxy, phenyl, $C_{1-6}$-alkoxy or $C_{1-6}$-alkoxy-$C_{1-6}$-alkyl, or

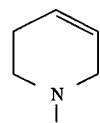
(c)

which may be optionally substituted with $C_{1-6}$-alkyl, $C_{2-6}$-alkenyl, $C_{2-6}$-alkynyl, phenoxy, phenylthio, phenyl, $C_{1-6}$-alkoxy or $C_{1-6}$-alkoxy-$C_{1-6}$-alkyl.

In certain examples, the group $R^1$ can contain one or more asymmetric carbon atoms in addition to those asymmetric centres already present in the molecule. In examples where this is the case, this invention includes all resulting diastereoisomers and mixtures thereof.

Various salts of compounds of formula (I) can be prepared which can be considered physiologically acceptable. These include addition salts derived from inorganic or organic acids, for example, acetates, fumarates, glutarates, glutaconates, lactates, maleates, methanesulphonates, phosphates, salicylates, succinates, sulphates, sulphamates, tartrates and paratoluenesulphonates. In some cases, solvates of either the free nucleosides or the acid addition salts can be isolated and these solvates may, for example, be hydrates or alcoholates.

Compounds of formula (I), which act as adenosine receptor agonists, are found to be useful in the treatment of central nervous system conditions such as anxiety, neuronal ischaemia/anoxia, convulsive disorders (epilepsy) and neurodegeneration (including Parkinson's disease). This includes treating disorders where the blood flow to the brain is interrupted, for example during traumatic head injury, cardiac arrest and stroke.

Further, the compounds of formula (I) are found to be useful as analgesic agents, in lowering plasma FFA levels or as cardiovascular agents.

The invention also relates to methods of preparing the above mentioned compounds. These methods comprise:

Method A

A compound of formula (I) may be prepared by reacting a substance of formula (II), wherein L represents a leaving group such as a halogen atom (e.g. a chlorine or bromine, atom) or a trimethylsilyloxy group, $R^2$ and $R^3$ are the same or different and represent hydrogen or a protecting group such as benzoyl-, p-toluoyl-, lower alkanoyl- (e.g. acetyl-), a 2,3-O-(1-methyl)ethylidene group or a substituted silyl group (e.g. a trimethylsilyl or t-butyldimethylsilyl group) with a hydrazine derivative of general formula (III)

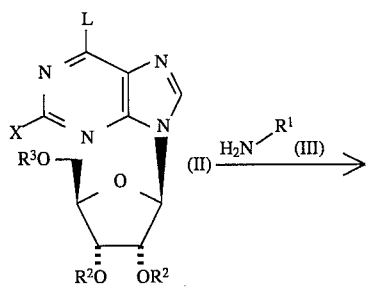

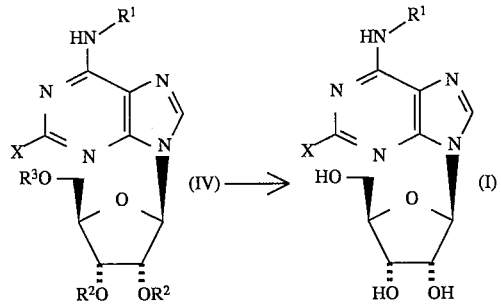

giving the compound of formula (IV) as the reaction product. In cases where R² and R³ are not hydrogen an additional step will be required to remove protecting groups from (IV); in cases where the groups R² and R³ are for example acetyl or benzoyl, suitable conditions for deprotection include methanolic ammonia, an alkali metal carbonate in methanol, an alkali metal alkoxide in the corresponding alcohol. Where the protecting groups are for example alkylsilicon or arylsilicon derivatives, suitable deprotection methods include for example treatment with tetraalkylammonium fluorides or aqueous hydrolysis in the presence of acid or base.

Method B

A compound of formula (I) (wherein X represents —NH—R⁴, or —O—R⁴, where R⁴ is $C_{1-6}$-alkyl) may be prepared by reacting a substance of general formula (V)

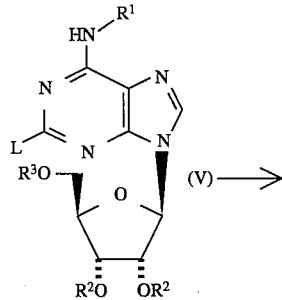

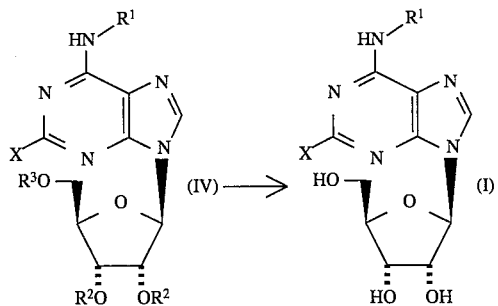

(where L is a leaving group as defined in method (A)) with a nucleophile, for example $C_{1-6}$-alkylamino (optionally in the presence of a suitable base) or with the anion ($C_{1-6}$-alkoxide or $C_{1-6}$-thioalkoxide) to afford the product (IV). In cases where R² and R³ are hydrogen, compound (I) can be obtained directly. However, in cases where R² and R³ are not hydrogen an additional step will be involved to remove protecting groups from (IV); examples of conditions for removal of protecting groups are given in process (A). In some reactions involving (V) with the anion ($C_{1-6}$-alkoxide or $C_{1-6}$-thioalkoxide), where R² and R³ are for example acetyl- or benzoyl-, partial or full deprotection may take place. In cases where only partial, deprotection has taken place, deprotection can be completed under conditions exemplified in method (A).

Method C

A compound of formula (I) may be prepared by reacting a substance of the general formula (VI) (where B represents —NH—R¹ or L as defined previously) with a diazotizing agent (such as, for example, 3-methylbutyl nitrite) to form an intermediate species which can be reacted further with a variety of substrates as exemplified below in order to introduce the group -X into the product (VII).

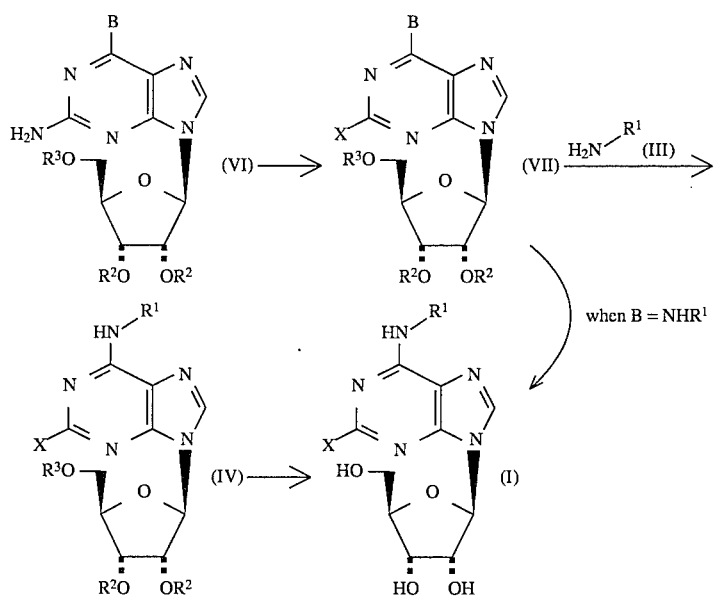

In the case where B represents a leaving group L, a further displacement reaction with for example (III) will be required in order to obtain the product (IV). In cases where the groups $R^2$ and $R^3$ are not hydrogen, or not all hydrogen, another step will be required to remove protecting groups from (IV); conditions for removing protecting groups are described in method A.

Methods for assessing adenosine receptor binding in vitro have been reviewed [Adenosine Receptors, (Cooper, D. M. F. and Londos, C., eds.) Alan R. Liss, Inc., New York, 1988, 43–62].

Evaluation of these compounds in established animal models has indicated that the compounds according to the invention possess desirable central nervous system properties. For example, they act as anticonvulsant agents, are effective in animal models of pain, and show cerebroprotective effects in laboratory test animals subjected to simulated cerebral ischaemia. In addition, the compounds may have efficacy as neuroprotective agents in cases of cerebral oedema and traumatic head injury.

Evaluation of in vitro binding to adenosine A1 and A2 receptors

The affinity of the novel compounds described in this invention for the adenosine A1 receptor was determined essentially as described in the literature using [$^3$H]-L-PIA as a radioligand (Naunyn-Schmiedeberg's Archives of Pharmacology, 1980, 313, 179–187). Affinity for the A2 receptor was measured using the radioligand [$^3$H]-CGS 21680 (European Journal of Pharmacology, 1989, 168, 243–246), and the values for representative compounds is given in the table below. In vitro receptor binding values obtained for the reference standards CFA [N-(cyclopentyl)adenosine] and L-PIA [N-(1-phenyl-2-propyl)adenosine] are included for comparison.

DMCM INDUCED SEIZURES IN MICE, I. P. 30 min.
Method description
DMCM, 15 mg/kg, i.p., clonic convulsions
RATIONALE
DMCM is an inverse agonist at the benzodiazepine receptor, presumably producing seizures by decreasing the potency of inhibition of the GABA receptor/benzodiazepine receptor/chloride ionophore complex (1).

METHODS
15 mg/kg of DMCM dissolved in 0.02 N HCl (1 mg/ml) is administered i.p. in a volume of 300 µl to male NMRI mice weighing 20±2 g. This induces two different responses: a) some animals manifest a brief loss of righting reflexes or take up an upright position in which they have a mild short clonus of the upper extremities, b) other animals manifest intense clonic and tonic convulsions of all extremities often followed by death. DMCM is administered 30 min. after an intraperitoneal injection of a test compound. The latency time for the presence of intense clonic and tonic convulsions and death is noted until 15 min. after administration of DMCM. At least 5 doses of each test compound are tested with 8 mice per dose.

RESULTS
An anticonvulsive $ED_{50}$ value is determined as the dose (mg/kg) protecting 50% of the animals against clonic convulsions. This method is described in more detail in Eur. J. Pharmacol. 94, 117–124, 1983.

The results obtained by testing compounds disclosed in the present invention are shown in the following table I.

TABLE I

| Adenosine agonist tested | A1 Receptor Binding (Ki, nM) | A2 Receptor Binding (Ki, nM) | Ratio A2/A1 | DMCM-ind. seizures ($ED_{50}$, mg/kg) |
|---|---|---|---|---|
| Example 5 | 4 | 691 | 173 | 0.1 |
| Example 9 | 4 | 1143 | 289 | 0.7 |
| Example 16 | 11 | 1733 | 158 | 1.0 |
| Example 17 | 1.4 | 1200 | 857 | 0.9 |
| CPA | 1.6 | 173 | 108 | 0.2 |
| L-PIA | 2 | 134 | 67 | 0.1 |

The compounds of the invention, together with a conventional adjuvant, carrier, or diluent, and if desired in the form of a pharmaceutically acceptable acid addition salt thereof, may be placed into the form of pharmaceutical compositions and unit dosages thereof, and in such form may be employed as solids, such as tablets of filled capsules, or liquids, such as solutions, suspensions, emulsions, elixirs, or capsules filled with the same, all for oral use, in the form of suppositories for rectal administration; or in the form of sterile injectable solutions for parenteral use (including subcutaneous administration and infusion). Such pharmaceutical compositions and unit dosage forms thereof may comprise conventional ingredients in conventional proportions, with or without additional active compounds or principles, and such unit dosage forms may contain any suitable effective amount of the adenosine receptor agonist commensurate with the intended daily dosage range to be employed. Tablets containing ten (10) milligrams of active ingredient or, more broadly, ten (10) to hundred (100) milligrams, per tablet, are accordingly suitable representative unit dosage forms.

The compounds of this invention can thus be used for the formulation of pharmaceutical preparation, e.g. for oral and parenteral administration to mammals including humans, in accordance with conventional methods of galenic pharmacy.

Conventional excipients are such pharmaceutically acceptable organic or inorganic carrier substances suitable for parenteral or enteral application which do not deleteriously react with the active compounds.

Examples of such carriers are water, salt solutions, alcohols, polyethylene glycols, polyhyroxyethoxylated castor oil, gelatine, lactose, amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxiliary agents, emulsifiers, salt for influencing osmotic pressure, buffers and/or colouring substances and the like, which do not deleteriously react with the active compounds.

For parenteral application, particularly suitable are injectable solutions or suspensions, preferably aqueous solutions with the active compound dissolved in polyhydroxylated castor oil.

Ampoules are convenient unit dosage forms.

Tablets, dragees, or capsules having talc and/or a carbohydrate carrier or binder or the like, the carrier preferably being lactose and/or corn starch and/or potato starch, are particularly suitable for oral application. A syrup, elixir or the like can be used in cases where a sweetened vehicle can be employed.

Generally, the compounds of this invention are dispensed in unit form comprising 0.05–100 mg in a pharmaceutically acceptable carrier per unit dosage.

The dosage of the compounds according to this invention is 0.1–300 mg/day, preferably 10–100 mg/day, when administered to patients, e.g. humans, as a drug.

A typical tablet which may be prepared by conventional tabletting techniques contains:

| Active compound | 5.0 mg |
| Lactosum | 67.0 mg Ph.Eur. |
| Avicel ™ | 31.4 mg |
| Amberlite ™ IRP 88 | 1.0 mg |
| Magnesii stearas | 0.25 mg Ph.Eur. |

As a result of their activity against pain or convulsive disorders and prevention of neurodegeneration under conditions of anoxia/ischaemia the compounds of the invention are extremely useful in the treatment of related symptoms in mammals, when administered in an amount effective for agonist activity of compounds of the invention. The compounds of the invention may accordingly be administered to a subject, e.g., a living animal body, including a human, in need of adenosine receptor agonist, and if desired in the form of a pharmaceutically acceptable acid addition salt thereof (such as the hydrobromide, hydrochloride, or sulphate, in any event prepared in the usual or conventional manner, e.g., evaporation to dryness of the free base in solution together with the acid), ordinarily concurrently, simultaneously, or together with a pharmaceutically acceptable carrier or diluent, especially and preferably in the form of a pharmaceutical composition thereof, whether by oral, rectal, or parenteral (including subcutaneous) route, in an effective amount of adenosine receptor agonist, and in any event an amount which is effective for the treatment of anoxia, traumatic injury, ischaemia, migraine or other pain symptoms, epilepsy, or neurodegenerative diseases owing to their adenosine receptor agonist activity. Suitable dosage ranges are 1–200 milligrams daily, 10–100 milligrams daily, and especially 30–70 milligrams daily, depending as usual upon the exact mode of administration, form in which administered, the indication toward which the administration is directed, the subject involved and the body weight of the subject involved, and the preference and experience of the physician or veterinarian in charge.

The preparation of compounds of formula (I) and preparations containing them is further illustrated in the following examples.

Hereinafter, TLC is thin layer chromatography, THF is tetrahydrofuran, TFA is trifluoracetic acid and m.p. is melting point. Where melting points are given, these are uncorrected. The structures of the compounds are confirmed by assignment of NMR spectra (from which representative peaks are quoted) and by microanalysis where appropriate. Compounds used as starting materials are either known compounds or compounds which can be prepared by methods known per se. Column chromatography was carried out using the technique described by Still, W. C. et al., Journal of Organic Chemistry, 1978, 43, 2923 on Merck silica gel 60 (Art 9385). HPLC was carried out on a Waters model 510 chromatograph interfaced via a system module to a Waters 490 multiwavelength detector to a reversed phase $C_{18}$ column (250×4 mm, 5 μm, 100 Å; eluent flow rate 1 mL/min. at 35° C.). Retention times are given in minutes.

EXAMPLE 1 (Method A)

2-Chloro-N-(4-morpholinyl)adenosine 2,6-Dichloro-9(H)-purine (5.8 g, 30.7 mmol) and 1-O-acetyl-2,3,5-tri-O-benzoyl-D-ribofuranose (16.26 g, 32.2 mmol) were thoroughly mixed and fused together at 145°–150° C. under oil pump vacuum. The resultant gummy mixture was stirred gently for 0.75 hours (during which time the acetic acid by-product evaporated), cooled to ca. 50° C. and dissolved in dichloromethane (100 ml) with stirring. This solution was applied directly to a column of silica gel (6×22 cm) and eluted initially with cyclohexane/dichloromethane (1/1), then with dichloromethane and finally with cyclohexane/ethyl acetate (1/1) to provide 2,6-dichloro-2,3,5-tri-O-benzoyl-β-D-ribofuranosyl-(9H)-purine (16.6 g, 87%) as a colourless foam, TLC $r_f$ 0.50 [$SiO_2$, cyclohexane/ethyl acetate (1/1)]. $^1$H NMR (400 MHz, $CDCl_3$) δ 4.72 (1H, dd, H-5'$_a$), 4.88 (1H, q, H-4'), 4.93 (1H, dd, H-5'$_b$), 6.15 (2H, m, H-2' & H-3'), 6.50 (1H, d, H-1'), 7.34–7.65 (9H, m, m- & p-ArH), 7.90–8.13 (6H, m, o-ArH), 8.28 (1H, s, H-8). (This method of preparation is similar to the one described by Imai, K-i. et al., Chemical and Pharmaceutical Bulletin, 1966, 14, 1377–1381, but without the use of a catalyst).

The above 2,6-dichloro-2,3,5-tri-O-benzoyl-β-D-ribofuranosyl-(9H)-purine (1.26 g, 2 mmol) and 4-aminomorpholine (0.89 g, 8.8 mmol) were dissolved in a mixture of dioxane (30 ml) and toluene (15 ml). The solution was heated at 50° C. for 20 hours after which time it was confirmed that the starting material was consumed and a new product was observed with TLC $r_f$ 0.20 [SiO$_2$, ethyl acetate/dichloromethane (4/1)]. The cooled reaction mixture was evaporated to a gum and coevaporated with methanol (20 ml). Dried potassium carbonate (0.55 g, 4 mmol) and methanol were added and stirring was continued for 20 hours, whereupon acetic acid (1.0 ml) was introduced. The reaction mixture was evaporated and the residue was coevaporated with toluene (30 ml) before purification by column chromatography on silica gel (2.5×20 cm). Elution with dichloromethane initially, gradually increasing the polarity of the eluent to a mixture of dichloromethane/ethanol/25% aqueous ammonia solution (100/10/1) provided the title compound (0.43 g, 55%) as semi-solid foam, TLC $r_f$ 0.24 [SiO$_2$, dichloromethane/ethanol/25% aqueous ammonia solution (60/10/1)], $^1$H NMR (400 MHz, Me$_2$SO-d$_6$) δ 3.56 (1H, m, H-5'a), 3.67 (1H, m, H-5'b), 3.95 (1H, q, H-4'), 4.14 (1H, m, H-3'), 4.51 (1H, q, H-2'), 5.84 (1H, d, H-1'), 8.43 (1H, s, H-8). This nucleoside could be recrystallised from ethyl acetate/trace ethanol to provide an analytical sample (0.3 g) as a white solid, m.p. 160°–161° C. (after drying in vacuo).

C$_{14}$H$_{19}$N$_6$ClO$_5$. H$_2$O requires C, 41.5; H, 5.2; N, 20.75; Cl, 8.75%. Found: C, 41.7; H, 5.35; N, 20.3; Cl, 8.6%.

EXAMPLE 2

2-Chloro-N-[1-(2,3,4,5,6,7-hexahydro)azepinyl]adenosine

The title compound was prepared according to method A as described in Example 1 and obtained as a foam (0.12 g, 62% from 2,6-dichloro-2,3,5-tri-O-benzoyl-β-D-ribofuranosyl-(9H)-purine); $^1$H NMR (400 MHz, Me$_2$SO-d$_6$) δ 3.55 (2H, 2m, H-5' and H-5'$_b$), 3.95 (1H, q, H-4'), 4.12 (1H, m, H-3'), 4.50 (1H, q, H-2'), 5.82 (1H, d, H-1'), 8.38 (1H, s, H-8). HPLC retention time 18.39 (gradient elution, 15–35% acentonitrile/0.1M pH 3.3 ammonium sulphate buffer: 214 nm detector); 99.9% purity.

EXAMPLE 3

2-Chloro-N-(2,6-dimethyl-1-piperidinyl)adenosine

The title compound was prepared according to method A as described in Example 1 and obtained as a foam (a mixture of diastereoisomers) (0.63 g, 61% from 2,6-dichloro-2,3,5-tri-O-benzoyl-β-D-ribofuranosyl-(9H)-purine); $^1$H NMR (400 MHz, Me$_2$SO-d$_6$) δ 3.55 (1H, m, H-5'$_a$), 3.65 (1H, m, H-5'$_b$), 3.95 (1H, m, H-4'), 4.12 (1H, m, H-3'), 4.55 (1H, q, H-2'), 5.82 (1H, 2d, H-1'), 8.35, 8.40 (1H, 2s, H-8). HPLC retention time 19.61 (gradient elution, 15–35% acetonitrile/0.1M pH 3.3 ammonium sulphate buffer: 214 nm detector).

EXAMPLE 4

2-Chloro-N-(4-methyl-1-piperazinyl)adenosine

The title compound was prepared according to method A as described in Example 1 and obtained as a foam (0.2 g, 14% from 2,6-dichloro-2,3,5-tri-O-benzoyl-β-D-ribofuranosyl-(9H)-purine); $^1$H NMR (400 MHz, Me$_2$SO-d$_6$) δ 3.56 (1H, m, H-5'$_a$), 3.67 (1H, m, H-5'$_b$), 3.96 (1H, m, H-4'), 4.13 (1H, m, H-3'), 4.50 (1H, m, H-2'), 5.84 (1H, d, H-1'), 8.40 (1H, s, H-8). HPLC retention time 10.00 (gradient elution, 15–35% acetonitrile/0.1M pH 3.3 ammonium sulphate buffer: 214 nm detector).

EXAMPLE 5

2-Chloro-N-(1-piperidinyl)adenosine 2,6-Dichloro-2,3,5-tri-O-benzoyl-β-D-ribofuranosyl-(9H)-purine (20.0 g, 31.7 mmol) (prepared as described in example 1), 1-aminopiperidine (6.35 g, 63.4 mmol) and N,N-diisopropylethylamine (8.20 g, 63.4 mmol) were dissolved in dioxane (300 ml), and after 2.5 hours TLC indicated that the starting material was consumed. Dichloromethane (500 ml) was added and the mixture was washed with water (2×150 ml). The organic phase was dried (MgSO$_4$) and evaporated in vacuo to a foam. The foam was treated with methanol (120 ml) (causing crystallisation) and the vessel was kept at −10° C. for 1 hour. The product, 2',3',5'-tri-O-benzoyl-2-chloro-N-(1-piperidinyl)adenosine, was collected as white crystals (19.4 g, 88%), m.p. 110°–112° C.; $^1$H NMR (400 MHz, Me$_2$SO-d$_6$) δ 4.68 (1H, dd, H-5'$_a$), 4.80 (1H, dd, H-5'$_b$), 4.88 (1H, q, H-4'), 6.20 (1H, t, H-3'), 6.50 (1H, d, H-1'), 6.85 (1H, t, H-2'), 8.45 (1H, s, H-8).

C$_{36}$H$_{33}$N$_6$ClO$_7$. H$_2$O requires C, 60.45; H, 4.9; N, 11.75%. Found: C, 60.45; H, 4.8; N, 11.3%.

The above 2',3',5'-tri-O-benzoyl-2-chloro-N-(1-piperidinyl)adenosine (19.2 g, 27.5 mmol) was dissolved in methanolic ammonia (150 ml) (previously saturated at −10° C.) and stirred at room temperature for 18 hours. The precipitated benzamide was removed by filtration, and the filtrate was evaporated to a fawn oil, which was triturated with diethyl ether to provide the title compound (6.0 g, 57%) as a white foam, $^1$H NMR (400 MHz, Me$_2$SO-d$_6$) δ 3.55 (1H, m, H-5'$_a$), 3.66 (1H, m, H-5'$_b$), 3.94 (1H, q, H-4'), 4.12 (1H, m, H-3'), 4.50 (1H, q, H-2'), 5.82 (1H, d, H-1'), 8.40 (1H, s, H-8); HPLC retention time 26.57 (gradient elution, 5–25% acetonitrile/0.1M pH 3.3 ammonium sulphate buffer: 214 nm detector); purity 99%.

EXAMPLE 6

2-Chloro-N-(2-phenyl-1-piperidinyl)adenosine

The title compound was prepared according to method A as described in Example 1 was obtained as a solid (0.25 g, 26%) by the reaction of 1-amino-2-phenylpiperidine (Overberger, C. G. and Herin, L. P. Journal of Organic Chemistry, 1962, 27, 417) with 9-(2',3',5'-tri-O-benzoyl-β-D-ribofuranosyl)-2,6-dichloro-9H-purine, followed by deprotection (as described in Example 5) to give the title nucleoside (a ca. 60:40 mixture of diastereoisomers): m.p. 186°–210° C.; $^1$H NMR (400 MHz, Me$_2$SO-d$_6$) δ 3.47–3.20 (2H, m, 5'-CH$_2$), 3.82–3.97, 4.04–4.14 (2H, 2m, H-3' and H-4'), 4.46–4.56 (1H, 2q, H-2'), 5.33, 5.73 (1H, 2d, H-1'), 8.26, 8.48 (1H, 28, H-8).

EXAMPLE 7

(R)-2-Chloro-N-[2-(methoxymethyl)-1-pyrrolidinyl]adenosine

The title compound was prepared as described in Example 5 and obtained as a semi-solid foam (0.49 g, 37% from 9-(2',3',5'-tri-O-benzoyl-β-D-ribofuranosyl)-2,6-dichloro-9H-purine); $^1$H NMR (400 MHz, Me$_2$SO-d$_6$) δ 3.56 (1H, m, H-5'$_a$), 3.67 (1H, m, H-5'$_b$), 3.95 (1H, q, H-4'), 4.13 (1H, 1, H-3'), 4.53 (1H, q, H-2'), 5.82 (1H, d, H-1'), 8.40 (1H, s, H-8); HPLC retention time 5.6 (gradient elution, 20–80% acetonitrile/water (containing 0.1% TFA): 250 nm detector); purity 99%.

EXAMPLE 8

(S)-2-Chloro-N-[2-(methoxymethyl)-1-pyrrolidinyl]adenosine

The title compound was prepared as described in Example 5 and obtained as a foam (0.66 g, 50% from 9-(2',3',5'-tri-O-benzoyl-β-D-ribofuranosyl)-2,6-dichloro-9H-purine); $^1$H NMR (400 MHz, Me$_2$SO-d$_6$) δ 3.56 (1H, m, H-5'$_a$), 3.67 (1H, m, H-5'$_b$), 3.95 (1H, q, H-4'), 4.13 (1H, q, H-3'), 4.53 (1H, q, H-2'), 5.82 (1H, d, H-1'), 8.40 (1H, s, H-8); HPLC retention time 5.6 (gradient elution, 20–80% acetonitrile/water (containing 0.1% TFA): 250 nm detector); purity 98%.

EXAMPLE 9 (Method C)

2-Fluoro-N-(1-piperidinyl)adenosine 9-(2',3',5'-Tri-O-acetyl-β-D-ribofuranosyl)-2-amino-6-chloro-(9H)-purine (6.0 g, 14 mmol) (prepared as described by Robins, M. J. and Uznanski, B., in Nucleic Acid Chemistry (Townsend, L. B. and Tipson, R. S., eds.,) John Wiley and Sons, Inc., 1986, 3, 144) was dissolved in dioxan (100 ml). 1-Aminopiperidine (1.83 ml, 16.95 mmol) was added followed by triethylamine (2.33 ml, 18.5 mmol) and the solution was stirred for 190 hours at room temperature. The reaction mixture was filtered, evaporated and the resultant residue was purified by column chromatography on silica gel eluting with ethyl acetate/cyclohexane (3/1) to afford 2',3',5'-tri-O-acetyl-2-amino-N-(1-piperidinyl)adenosine (4.88 g, 71%) as a foam which solidified on coevaporation with methanol: m.p. 77°–790° C. $^1$H NMR (400 MHz, Me$_2$SO-d$_6$) δ 2.04 (6H, s, 2' and 3'-O-acetyl-CH$_3$), 2.13 (3H, s, 5'-O-acetyl-CH$_3$), 4.30 (2H, m, H-5'$_a$ and H-4'), 4.40 (1H, dd, H-5'$_b$), 6.03 (1H, d, H-1').

The above 2',3',5'-tri-O-acetyl-N-(1-piperidinyl)adenosine (1.33 g, 2.7 mmol) was dissolved in THF (50 ml) and the temperature of the solution was held between −10° C. and −20° C. Fluoroboric acid (48%, 100 ml) was added followed by an aqueous solution of sodium nitrite (0.75 g/ml, 1.5 ml). Addition of three identical amounts of sodium nitrite was continued at 0.3 hour intervals, after which TLC investigation (on a neutralised sample) indicated that the starting material was consumed [r$_f$ 0.47 (SiO$_2$, ethyl acetate/methanol (90/10))]. The pH of the reaction mixture was adjusted to ca. 6 with 50% sodium hydroxide solution with cooling to below 0° C. and the now red reaction mixture was diluted with water (250 ml). The solution was extracted with chloroform (2×100 ml) and the combined extracts were dried (MgSO$_4$). The residue on evaporation (containing 2',3',5'-tri-O-acetyl-2-fluoro-N-(1-piperidinyl)adenosine was treated with methanolic ammonia (150 ml) (previously saturated at −10° C.) and stirred at room temperature for 72 hours. The reaction mixture was evaporated and the resultant residue was purified by column chromatography on silica gel eluting with dichloromethane/methanol (0–10%) to provide the title compound (0.093 g) as a white solid, after washing with ethyl acetate. M.p. 197°–199° C.; $^1$H NMR (400 MHz, Me$_2$SO-d$_6$) δ 3.57, 3.65 (2H, ABX, H-5'$_a$ and H-5'$_b$), 3.92 (1H, q, H-4'), 4.12 (1H, m, H-3'), 4.50 (1H, q, H-2'), 5.80 (1H, d, H-1'), 8.35 (1H, s, H-8). HPLC retention time 10.12 (gradient elution, 5–25% acetonitrile/0.1M pH 3.3 ammonium sulphate buffer: 214 nm detector): 100% purity.

C$_{15}$H$_{21}$FN$_6$O$_4$. O.2 EtOAc requires C, 49.2; H, 5.9; N, 21.8%. Found: C, 49.2; H, 5.9; N, 21.75%.

EXAMPLE 10 (Method C)

2-Bromo-N-(1-piperidinyl)adenosine 9-(2',3',5'-Tri-O-acetyl-β-D-ribofuranosyl)-2-amino-6-chloro-9H-purine (2.2 g, 5.13 mmol) (prepared as described in example 9) was dissolved in acetonitrile (40 ml).

Bromoform (5.5 ml, 62.9 mmol) (dried by passage through an alumina column) and 3-methylbutylnitrite (6.1 ml, 45.6 mmol) were introduced and the reaction mixture was saturated with nitrogen before being heated at 45° C. for 18 hours and allowed to cool to room temperature; the product had r$_f$ 0.47 (SiO$_2$, ethyl acetate). The reaction mixture was evaporated in vacuo and purified by flash chromatography on silica gel; elution initially with dichloromethane followed by dichloromethane/methanol (50:1) provided the product which was dissolved in a mixture of dichloromethane (2 ml) and ethanol (30 ml). The dichloromethane was removed in vacuo and 9-(2',3',5'-tri-O-acetyl-β-D-ribofuranosyl)-2-bromo-6-chloro-9H-purine crystallized as a solid (2.11 g, 42%): m.p. 160°–162° C.

To a sample of 9-(2',3',5'-tri-O-acetyl-β-D-ribofuranosyl)-2-bromo-6-chloro-9H-purine (1.0 g, 2.03 mmol) in dioxan (20 ml) 1-aminopiperidine (0.24 ml, 2.23 mmol) was added followed by triethylamine (2.33 ml, 18.5 mmol) and the solution was stirred for 20 hours at room temperature. The reaction mixture was filtered, evaporated and the resultant residue was purified by flash chromatography on silica gel. Elution initially with dichloromethane and then with dichloromethane/methanol (100:1) provided impure 2',3',5'-tri-O-acetyl-2-bromo-N-(1-piperidinyl)adenosine which was repurified by flash chromatography in cyclohexane/ethyl acetate (1:1), giving the pure product as a foam (0.86 g, 76%).

The above 2',3',5'-tri-O-acetyl-2-bromo-N-(1-piperidinyl)adenosine was treated with methanolic ammonia (10 ml) (previously saturated at −10° C.) and stirred at room temperature for 16 hours after which time TLC investigation indicated that the starting material was consumed and a new product was present [r$_f$ 0.24 (SiO$_2$, ethyl acetate/methanol (90/10)]. The reaction mixture was evaporated and the resultant residue was treated with water (25 ml) and the suspension was extracted with ethyl acetate (2×25 ml). The combined extracts were dried (MgSO$_4$) and coevaporated with dichloromethane; $^1$H NMR (400 MHz, Me$_2$SO-d$_6$) δ 3.54, 3.65 (2H, ABX, H-5'$_a$ and H-5'$_b$), 3.94 (1H, q, H-4'), 4.12 (1H, m, H-3'), 4.50 (1H, m, H-2'), 5.82 (1H, d, H-1'), 8.38 (1H, s, H-8). HPLC retention time 14.25 (gradient elution, 5–25% acetonitrile/0.1M pH 3.3 ammonium sulphate buffer: 214 nm detector).

C$_{15}$H$_{21}$BrN$_6$O$_4$. 0.33 CH$_2$Cl$_2$. 0.75 H$_2$O requires C, 40.1; H, 5.1; N, 18.3%. Found: C, 40.5; H, 5.2; N, 17.8%.

EXAMPLE 11 (Method C)

2-Iodo-N-(1-pyrrolidinyl)adenosine 9-(2',3',5'-Tri-O-acetyl-β-D-ribofuranosyl)-2-amino-6-chloro-9H-purine (2.2 g, 5.13 mmol) (prepared as described in Example 9) (0.54 g, 1.0 mmol) was dissolved in dioxan (5 ml). 1-Aminopyrrolidine hydrochloride (0.135 g, 1.1 mmol) was added followed by triethylamine (0.312 ml, 2.3 mmol) and the solution was stirred for 72 hours at room temperature. Further 1-aminopyrrolidine hydrochloride (0.405 g, 3.3 mmol) and triethylamine (0.935 ml, 3.45 mmol) were introduced and stirring was continued at room temperature for 24 hours. Ethanol (1 ml) was added and the solution was heated at 50° C. for 2 hours. The reaction mixture was evaporated and purified by column chromatography on silica gel eluting initially with n-heptane/THF (4/1) and later with n-heptane/ THF (1/1) to provide 9-(2',3',5'-tri-O-acetyl-β-D-ribofuranosyl)-2-iodo-6-(1-pyrrolidinyl)-(9H)-purine (0.14 g, 23%) as a solid which was recrystallized from ethanol giving 0.08 g (14%); $^1$H NMR (400 MHz, Me$_2$SO-d$_6$) δ 2.04, 2.07 (6H, s, 2'- and 3'-O-acetyl-CH$_3$), 2.13 (3H, s, 5'-O-acetyl-CH$_3$), 4.28 (1H, m, H-5'$_a$), 4.35–4.43 (2H, m, H-5'$_b$ and H-4'), 6.15 (1H, d, H-1'), 8.29 (1H, s, H-8).

The above 9-(2',3',5'-tri-O-acetyl-β-D-ribofuranosyl)-2-iodo-6-(1-pyrrolidinyl)-(9H)-purine (0.063 g, 0.107 mmol) was suspended in methanol (1 ml) and dried potassium carbonate (0.030 g, 0.22 mmol) was introduced. The reaction mixture was stirred for 24 hours at room temperature and further portions of methanol (10 ml) and dried potassium carbonate (0.030 g, 0.22 mmol) were added. After a further 24 hours, the solution was treated with glacial acetic acid (0.1 ml) and evaporated. The residue was dissolved in a mixture of water (20 ml) and methanol (10 ml) and the methanol was removed by azeotropic distillation, causing the product to crystallize. The title compound was obtained as white crystals, m.p. 216°–217° C.; $^1$H NMR (400 MHz, Me$_2$SO-d$_6$) δ 3.94 (1H, q, H-4'), 4.12 (1H, q, H-3'), 4.50 (1H, q, H-2'), 5.83 (1H, d, H-1'), 8.28 (1H, s, H-8); HPLC retention time 13.70 (gradient elution, 25–45% acetonitrile/0.1M Ph 3.3 ammonium sulphate buffer: 214 nm detector): purity 97.5%.

EXAMPLE 12 (Method B)

N-(1-Piperidinyl)-2-(1-propoxy)adenosine

2-Chloro-N-(1-piperidinyl)adenosine (0.50 g, 1.3 mmol) (Example 5) was dissolved in a solution of sodium hydroxide (0.51 g, 1.3 mmol) in 1-propanol (15 ml), and the solution was heated at reflux for 4.5 hours, after which time TLC investigation showed that the starting material had been consumed. The reaction mixture was evaporated and the resultant residue was dissolved in water. The solution was neutralized with 4N aqueous hydrochloric acid and extracted with dichloromethane (3×50 ml). The combined extracts were dried (MgSO$_4$) and evaporated to an oil which was triturated with diethyl ether to afford a fawn foam. This foam was purified by column chromatography on silica gel (2×20 cm); elution with a mixture of dichloromethane/ ethanol 25% aqueous ammonia solution (60/10/1) provided the title compound (0.20 g, 37%) as a semi-solid foam; $^1$H NMR (400 MHz, Me$_2$SO-d$_6$) δ 3.54, 3.65 (2H, ABX, H-5'$_a$ and H-5'$_b$), 3.92 (1H, q, H-4'), 4.15 (1H, q, H-3'), 4.60 (1H, q, H-2'), 5.80 (1H, d, H-1'), 8.16 (1H, s, H-8).

EXAMPLE 13

2-Chloro-N-(4-phenyl-1-piperazinyl)adenosine

The title compound was prepared according to method A as described in Example 6 by reacting 1-amino-4-phenylpiperazine hydrochloride (also prepared using the method described by Overberger, C. G. and Herin, L. P., Journal of Organic Chemistry, 1962, 27, 417) (0.77 g, 3.0 mmol) with 9-(2',3',5'-tri-O-benzoyl-β-D-ribofuranosyl)-2,6-dichloro-9H-purine (1.90 g, 3.0 mmol), followed by debenzoylation of the purified product using methanolic ammonia. This provided the title 2-chloro-N-(4-phenyl-1-piperazinyl)adenosine (0.81 g, 60%) (after column chromatography as a foam, $^1$H NMR (DMSO-d$_6$) δ 3.53–3.60 (1H, m, H-5'$_a$), 3.63–3.70 (1H, m, H-5'$_b$), 3.95 (1H, q, H-4'), 4.13 (1H, q, H-3'), 4.51 (1H, q, H-2'), 5.07 (1H, t, 5'-OH), 5.22, 5.50 (2H, 2d, 2'- and 3'-OH), 5.85 (1H, d, H-1'), 6.77–7.26 (5H, 3m, Ar—H), 8.44 (1H, s, H-8), 9.50 (1H, s, N—H).

C$_{20}$H$_{24}$ClN$_7$O$_4$. H$_2$O requires C, 50.1; H, 5.3; N, 20.4%. Found: C, 50.2; H, 5.4; N, 20.0%.

EXAMPLE 14

2-Chloro-N-(4-phenyl-1,2,3,6-tetrahydro-1-pyridinyl)adenosine

The title compound was prepared according to method A as described above by reacting crude 1-amino-4-phenyl-1,2,3,6-tetrahydropyridine (prepared by the procedure outlined in Example 6) (1.25 g) with 9-(2',3',5'-tri-O-benzoyl-β-D-ribofuranosyl)-2,6-dichloro-9H-purine (2.50 g, 3.9 mmol), followed by debenzoylation of the purified product using methanolic ammonia to provide the title 2-Chloro-N-(4-phenyl-1,2,3,6-tetrahydro-1-pyridinyl)adenosine (0.20 g 12%) (after column chromatography) as a foam, $^1$H NMR (DMSO-d$_6$) δ 3.53–3.70 (4H, m, H-5'$_a$, H-5'$_b$ and —CH$_2$—), 3.94 (1H, q, H-4'), 4.14 (1H, q, H-3'), 4.52 (1H, q, H-2'), 5.07 (1H, t, 5'-OH), 5.22, 5.50 (2H, 2d, 2'- and 3'-OH), 5.85 (1H, d, H-1'), 6.15 (1H, br s, vinylic C—H), 7.24–7.51 (5H, m, Ar—H), 8.43 (1H, s, H-8), 9.55 (1H, s, N—H).

C$_{21}$H$_{23}$ClN$_6$O$_4$, 1.25H$_2$O requires C, 52.4; H, 5.3; N, 17.5%. Found: C, 52.6; H, 5.0; N, 17.1%.

EXAMPLE 15

2-Chloro-N-(4-phenyl-1-piperidinyl)adenosine

The title compound was prepared according to method A as described above by reacting 1-amino-4-phenylpiperidine (prepared as outlined in Example 6) (0.77 g, 3.6 mmol) with 9-(2',3',5'-tri-O-benzoyl-β-D-ribofuranosyl)-2,6-dichloro-9H-purine (1.90 g, 3.0 mmol), followed by debenzoylation of the purified product using methanolic ammonia. This provided the title 2-chloro-N-(4-phenyl-1-piperidinyl)adenosine (0.49 g, 37%) as a solid which precipitated on evaporation of column chromatography fractions, mp 142°–149° C. $^1$H NMR (DMSO-d$_6$) δ 3.53–3.60 (1H, m, H-5'$_a$), 3.63–3.70 (1H, m, H-5'$_b$), 3.95 (1H, q, H-4'), 4.13 (1H, q, H-3'), 4.51 (1H, q, H-2'), 5.07 (1H, t, 5'-OH), 5.22, 5.50 (2H, 2d, 2'- and 3'-OH), 5.84 (1H, d, H-1'), 7.18–7.35 (5H, 2m, Ar—H), 8.43 (1H, s, H-8) 9.45 (1H, s, N—H).

C$_{21}$H$_{25}$ClN$_6$O$_4$ requires C, 54.6; H, 5.8; N, 17.4%. Found: C, 54.4; H, 5.8; N, 17.0%.

EXAMPLE 16

2-Chloro-N-(3-phenoxy-1-piperidinyl)adenosine 1-(1,1-Dimethylethoxycarbonyl)-3-hydroxypiperidine 3-Hydroxypiperidine (10.1 g, 0.1 mol) was dissolved in tetrahydrofuran (50 ml) and 1N aqueous sodium hydroxide solution (95 ml) was introduced. The solution was cooled to 0° C. and a solution of di-tert-butyl dicarbonate (24.0 g, 0.11 mol) in tetrahydrofuran was added over 1 h. The reaction mixture was stirred at ambient temperature for 18 h and evaporated to an aqueous suspension. Water (100 ml) was added and the mixture was extracted with dichloromethane (3×100 ml). The combined extracts were dried (MgSO$_4$), evaporated and the residue was recrystallised from n-heptane to provide the title product as a solid (15.71 g, 78%), mp 67°–69° C.

3-Phenoxypiperidine 1-(1,1-Dimethylethoxycarbonyl)-3-hydroxypiperidine (6.0 g, 30 mmol) was dissolved in toluene (75 ml) and phenol (2.82 g, 30 mmol) was added followed by triphenylphosphine (11.8 g, 45 mmol). To this mixture a solution of diethylazodicarboxylate (7.84 g, 45 mmol) in toluene (75 ml) was introduced dropwise and the reaction mixture was stirred for 18 h. at ambient temperature during which time triphenylphosphine oxide precipitated. The reaction mixture was filtered, washed with 0.1N sodium hydroxide solution (55 ml), 0.5N sodium bicarbonate (100 ml) and with a mixture of saturated brine (25 ml) and water (25 ml). The dried toluene solution was evaporated, the residue was dissolved in ethyl acetate (10 ml) and cyclohexane (200 ml) was added. The solid precipitate was removed and the residue on evaporation was purified by flash chromatography on silica gel (7.5×15 cm). Elution with heptane ethyl acetate (9/1) provided the phenyl ether as an oil (4.01 g, 40%), containing the desired intermediate as well as ca. 20% phenol. This oil was dissolved in dichloromethane (15 ml) and trifluoroacetic acid (3 ml) was added. The solution was stirred at room temperature for 6 h and at –18° C. for 72 h. Saturated sodium bicarbonate solution was added to the reaction mixture until neutrality was reached, followed by extraction with dichloromethane (6×30 ml). The combined extracts were dried (MgSO$_4$) and evaporated to an oil which was dissolved in toluene (200 ml) containing methanol (1.26 ml, 30 mmol). Chlorotrimethylsilane (1.82 ml, 15 mmol) was added, and in the absence of crystallization, the solution was evaporated to an oil, which was treated with diethyl ether. The solid which was formed was dried in vacuo to give the title compound (1.90 g, 27%), mp 156°–159° C.

This 3-phenoxypiperidine was N-aminated using the method described in Example 6.

2-Chloro-N-(3-phenoxy-1-piperidinyl)adenosine was prepared according to method A as described in Example 6 by reacting 1-amino-3-phenoxypiperidine (0.60 g, 3.4 mmol) with 9-(2',3',5'-tri-O-benzoyl-β-D-ribofuranosyl)-2,6-dichloro-9H-purine (2.0 g, 3.2 mmol), followed by debenzoylation of the purified product using methanolic ammonia. This provided the desired compound (0.65 g, 43%) (after column chromatography) as a foam, $^1$H NMR (DMSO-d$_6$) δ 3.53–3.60 (1H, m, H-5'$_a$), 3.64–3.72 (1H, m, H-5'$_b$), 3.96 (1H, q, H-4'), 4.14 (1H, q, H-3'), 4.50–4.59 (1H, m, H-2' and —C—H) ), 5.07 (1H, t, 5'-OH), 5.23, 5.50 (2H, 2d, 2'- and 3'-OH), 5.84 (1H, d, H-1'), 6.79–7.32 (5H, 3m, Ar—H), 8.45 (1H, s, H-8), 9.55 (1H, s, N—H).

$C_{21}H_{25}ClN_6O_5$. 0.5 $H_2O$ requires C, 51.9; H, 5.4; N, 17.3%. Found: C, 51.9; H, 5.5; N, 17.1%.

EXAMPLE 17

2-Chloro-N-[4-phenoxy-1-piperidinyl]adenosine

This compound was prepared from 4-hydroxypiperidine using the methodology described in Example 16. 1-Amino-4-phenoxypiperidine (0.96 g, 5.0 mmol) was reacted with 9-(2',3',5'-tri-O-benzoyl-β-D-ribofuranosyl)-2,6-dichloro-9H-purine (2.50 g, 4 mmol), followed by debenzoylation of the purified product using methanolic ammonia. This provided the title 2-chloro-N-(4-phenoxy-1-piperidinyl)adenosine (1.07 g, 57%) as a foam, $^1$H NMR (DMSO-d$_6$) δ 3.52–3.60 (1H, m, H-5'$_a$), 3.63–3.70 (1H, m, H-5'$_b$), 3.95 (1H, q, H-4'), 4.14 (1H, q, H-3'), 4.43–4.54 (2H, m, H-2' and —C—H), 5.07 (1H, t, 5'-OH), 5.22, 5.50 (2H, 2d, 2'- and 3'-OH), 5.84 (1H, d, H-1'), 6.90–7.33 (5H, 2m, Ar—H), 8.42 (1H, s, H-8), 9.49 (1H, s, N—H).

$C_{21}H_{25}ClN_6O_4$. $H_2O$ requires C, 51.0; H, 5.5; N, 17.0%. Found: C, 50.9; H, 5.2; N, 16.6%.

EXAMPLE 18

2-Chloro-N-(3-phenylthio-1-piperidinyl)adenosine

3-Phenylthiopiperidine was prepared from 1-(1,1-dimethylethoxycarbonyl)-3-hydroxypiperidine by the method described by Kotsuki et al., Tetrahedron Letters, 1991, 32, 4155–4158; otherwise the synthesis proceeded as described in Example 16. 1-Amino-3-phenylthiopiperidine (0.98 g, 4.0 mmol) was reacted with 9-(2',3',5'-tri-O-benzoyl-β-D-ribofuranosyl)2,6-dichloro-9H-purine (2.11 g, 3.3 mmol), followed by debenzoylation of the purified product using methanolic ammonia. This provided the title 2-chloro-N-(3-phenylthio-1-piperidinyl)adenosine (0.89 g, 55%) as a foam, $^1$H NMR (DMSO-d$_6$) δ 3.52–3.59 (1H, m, H-5'$_a$), 3.63–3.71 (1H, m, H-5'$_b$) 3.95 (1H, q, H-4'), 4.13 (1H, q, H-3'), 4.46–4.54 (1H, q, H-2'), 5.07 (1H, t, 5'-OH), 5.22, 5.49 (2H, 2d, 2'- and 3'-OH), 5.84 (1H, d, H-1'), 7.20–7.50 (5H, 2m, Ar—H), 8.43 (1H, s, H-8), 9.50 (1H, s, N—H).

$C_{21}H_{25}ClN_6O_4$, 0.5 $H_2O$ requires C, 50.2; H, 5.2; N, 16.7%. Found: C, 50.0; H, 5.3; N, 16.6%.

EXAMPLE 19

2-Chloro-N-(4-phenylthio-1-piperidinyl)adenosine

The title compound was prepared as described in Example 18.

1-Amino-4-phenylthiopiperidine (1.10 g, 6.7 mmol) was reacted with 9-(2',3',5'-tri-O-benzoyl-β-D-ribofuranosyl)-2,6-dichloro-9H-purine (2.5 g, 4 mmol), followed by debenzoylation of the purified product using methanolic ammonia. This provided the title 2-chloro-N-(4-phenylthio- 1-piperidinyl)adenosine (1.25 g, 65%) as a foam, $^1$H NMR (DMSO-d$_6$) δ 3.51–3.60 (1H, m, H-5'$_a$), 3.62–3.68 (1H, m, H-5'$_b$), 3.95 (1H, q, H-4'), 4.14 (1H, q, H-3'), 4.50 (1H, q, H-2'), 5.08 (1H, t, 5'-OH), 5.21, 5.50 (2H, 2d, 2'- and 3'-OH), 5.83 (1H, d, H-1'), 7.24–7.45 (5H, 2m, Ar—H), 8.41 (1H, s, H-8), 9.44 (1H, s, N—H).

$C_{21}H_{25}ClN_6O_4S$, 0.75 $H_2O$ requires C, 49.8; H, 5.3; N, 16.6%. Found: C, 49.6; H, 5.2; N, 16.5%.

EXAMPLE 20

2-Chloro-N-[2-(phenylthiomethyl)-1-piperidinyl]adenosine 2-(Phenylthiomethyl)piperidine was prepared from 2-(hydroxymethyl)piperidine by the method described by Kotsuki et al., Tetrahedron Letters, 1991, 32, 4155–4158; otherwise the synthesis proceeded as described in Example 16. 1-Amino-2-(phenylthiomethyl)piperidine (1.4 g, 6.5 mmol) was reacted with 9-(2',3',5'-tri-O-benzoyl-β-D-ribofuranosyl)-2,6-dichloro-9H-purine (2.0 g, 3.25 mmol), followed by debenzoylation of the purified product using methanolic ammonia. This provided the title 2-chloro-N-[2-(phenylthiomethyl)-1-piperidinyl]adenosine (0.17 g, 10%) as a foam (a mixture of diastereoisomers); ¹H NMR (DMSO-d₆) δ 3.51–3.59 (1H, m, H-5'$_a$), 3.62–3.70 (1H, m, H-5'$_b$), 3.95 (1H, q, H-4'), 4.13 (1H, q, H-3'), 4.47–4.56 (1H, m, H-2'), 5.06 (1H, t, 5'-OH), 5.22, 5.50 (2H, 2d, 2'- and 3'-OH), 5.82–5.87 (1H, 2d, H-1'), 7.16–7.54 (5H, 2m, Ar—H), 8.41, 8.46 (1H, 2s, H-8), 9.40 (1H, s, N—H).

EXAMPLE 21

2-Chloro-N-(3-hydroxypiperidinyl)adenosine

The title compound was prepared according to method A as described above by reacting 1-amino-3-hydroxypiperidine (prepared from 3-hydroxypiperidine as outlined in Example 6) (0.60 g, 5.9 mmol) with 9-(2',3',5'-tri-O-benzoyl-β-D-ribofuranosyl)-2,6-dichloro-9H-purine (2.50 g, 3.94 mmol), followed by debenzoylation of the purified product using methanolic ammonia to provide the title 2-chloro-N-(3-hydroxypiperidinyl) adenosine (0.12 g, 8%) (after column chromatography) as a foam (a mixture of diastereoisomers); ¹H NMR (DMSO-d₆) δ 3.52–3.60 (1H, m, H-5'$_a$), 3.63–3.70 (1H, m, H-5'$_b$), 3.95 (1H, q, H-4'), 4.14 (1H, m, H-3'), 4.52 (1H, m, H-2'), 5.08 (1H, t, 5'-OH), 5.22, 5.50 (2H, 2d, 2'- and 3'-OH), 5.84 (1H, d, H-1'), 8.43 (1H, br s, H-8), 9.45 (1H, 2 br s, N—H).

EXAMPLE 22

2-Chloro-N-(4-phenylsulphonyl-1-piperidinyl)adenosine

2-Chloro-N-(4-phenylthio-1-piperidinyl)adenosine (Example 19) (0.25 g, 0.5 mmol) was dissolved in methanol (2 ml) and a solution of potassium hydrogen persulphate ("Oxone") (Trost, B. M. and Curran, D. P., Tetrahedron Letters, 1981, 22, 1287–1290) (0.47 g, 0.76 mmol) in water (2 ml) was added at 0° C. The yellowish reaction mixture was stirred at ambient temperature for 4 h., and saturated sodium bicarbonate (10 ml) was introduced. The suspension was extracted with dichloromethane (2×50 ml), and a yellow gum was seen to appear in the aqueous phase. This yellow gum was dissolved in methanol (20 ml), the dried dichloromethane extracts were added, and the mixture was evaporated to a residue. Purification by "flash" chromatography, eluting initially with dichloromethane, proceeding to dichloromethane/methanol (9/1) provided the title nucleoside as a foam (0.04 g, 15%), ¹H NMR (DMSO-d₆) δ 3.50–3.60 (1H, m, H-5'$_a$), 3.62–3.68 (1H, m, H-5'$_b$), 3.93 (1H, br q, H-4'), 4.12 (1H, m, H-3'), 4.50 (1H, m, H-2'), 5.05 (1H, t, 5'-OH), 5.21, 5.48 (2H, 2d, 2'- and 3'-OH), 5.82 (1H, d, H-1'), 7.66–7.94 (5H, 2m, Ar—H), 8.41 (1H, s, H-8), 9.49 (1H, s, N—H).

EXAMPLE 23 (Method C)

2-Methylthio-N-(1-piperidinyl)adenosine 9-(2',3',5'-Tri-O-acetyl-β-D-ribofuranosyl)-6-chloro-2-methylthio-9H-purine 9-(2',3',5'-Tri-O-acetyl-β-D-ribofuranosyl)-2-amino-6-chloro-9H-purine (see Example 9) (4.0 g, 9.3 mmol) was dissolved in acetonitrile (100 ml). Isoamylnitrite (10.84 g, 93 mmol) was introduced followed by methyl disulphide (4.14 ml, 46 mmol) and the reaction mixture was heated at an oil bath temperature of 100° C. for 2h. The evolved gas was removed via a hypochlorite scrubber. The reaction mixture was cooled, evaporated and purified by flash chromatography on silica gel. Elution initially with dichloromethane, followed by dichloro-methane/methanol (100/1) provided 9-(2',3',5'-tri-O-acetyl-β-D-ribofuranosyl)-6-chloro-2-methylthio-9H-purine (3.1 g, 72%) as a foam, ¹H NMR (CDCl₃) δ 2.12, 2.14, 2.18 (9H, 3s, 2', 3' and 5'-O-acetyl CH₃), 2.66 (3H, s, —SCH₃), 4.28–4.51 (3H, m, H-5'$_a$, H-5'$_b$ and H-4'), 5.66 (1H, t, H-3'), 6.0 (1H, t, H-2'), 6.13 (1H, d, H-1'), 8.11 (1H, s, H-8).

The above 9-(2',3',5'-tri-O-acetyl-β-D-ribofuranosyl)-6-chloro-2-methylthio-9H-purine (1.83 g, 3.9 mmol) was dissolved in dioxan (40 ml) followed by 1-aminopiperidine (0.59 g, 5.85 mmol) and triethyl-amine (1.63 ml, 11.7 mmol). The reaction mixture was stirred at ambient temperature for 18 h, evaporated and purified by flash chromatography on silica gel. Elution initially with dichloromethane, followed by dichloromethane/methanol (100/1) provided 9-(2',3',5'-tri-O-acetyl-β-D-ribofuranosyl)-2-methylthio-6-(1-piperidinyl)-9H-purine (1.24 g, 59%) as a foam. This compound was dissolved in methanolic ammonia (10 ml) and the solution was stirred at room temperature for 18 h, evaporated and purified by flash chromatography on silica gel. Elution initially with dichloromethane, followed by dichloromethane/methanol (19/1) gave 2-methylthio-N-(1-piperidinyl) adenosine (0.67 g, 55%) as a foam, ¹H NMR (DMSO-d₆) δ 2.51 (3H, s, —SCH₃), 3.50–3.56 (1H, m, H-5'$_a$), 3.62–3.68 (1H, m, H-5'$_b$) 3.92 (1H, q, H-4'), 4.15 (1H, q, H-3'), 4.50 (1H, q, H-2'), 5.03 (1H, t, 5'-OH), 5.18, 5.44 (2H, 2d, 2'- and 3'-OH), 5.84 (1H, d, H-1'), 8.24 (1H, s, H-8), 8.84 (1H, s, N—H).

$C_{16}H_{24}N_6O_4S.H_2O$ requires C, 46.4; H, 6.3; N, 20.3%. Found: C, 46.1; H, 6.0; N, 19.8%.

We claim:

1. A method of treating myocardial or cerebral ischemia, comprising administering to a person in need thereof an effective amount of a compound of formula I:

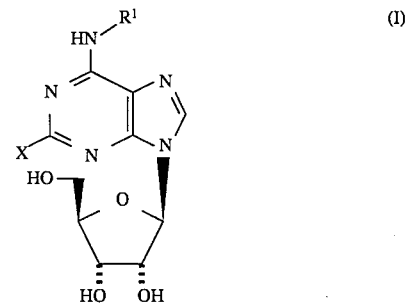

wherein

X is halogen, perhalomethyl, cyano, $C_{1-6}$-alkoxy, $C_{1-6}$-alkylthio or $C_{1-6}$-alkylamino;

R¹ is

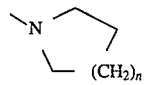

which is optionally substituted with one or two $C_{1-6}$-alkyl groups, $C_{2-6}$-alkenyl, $C_{2-6}$-alkynyl, phenoxy, phenylsulphonyl, phenylthio, hydroxy, phenyl, $C_{1-6}$-alkoxy or -$C_{1-6}$-alkyl-$C_{1-6}$-alkoxy, wherein n is 1; or a pharmaceutically acceptable salt thereof.

2. The method according to claim 1, wherein the compound is selected from the group consisting of (R)-2-Chloro-N-[2-(methoxymethyl)-1-pyrrolidinyl]adenosine;

(S)-2-Chloro-N-[2-(methoxymethyl)-1-pyrrolidinyl]adenosine;

2-Iodo-N-(1-pyrrolidinyl)adenosine; and pharmaceutically acceptable salts thereof.

3. A method of wearing myocardial or cerebral ischemia, comprising administering to a person in need thereof an effective amount of a compound of formula I:

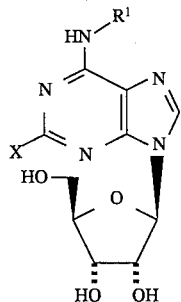

wherein

X is halogen, perhalomethyl, cyano, $C_{1-6}$-alkoxy or $C_{1-6}$-alkylthio;

$R^1$ is

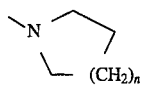

which is optionally substituted with one or two $C_{1-6}$-alkyl groups, $C_{2-6}$-alkenyl, $C_{2-6}$-alkynyl, phenoxy, phenylsulphonyl, phenylthio, hydroxy, phenyl, $C_{1-6}$-alkoxy, -$C_{1-6}$-alkyl-$C_{1-6}$-alkoxy or phenylthiomethyl, wherein n is 2; or a pharmaceutically acceptable salt thereof.

4. The method according to claim 3, wherein X is halogen.

5. The method according to claim 3, wherein $R^1$ is unsubstituted or substituted with phenoxy.

6. The method according to claim 3, wherein the compound is selected from the group consisting of 2-Chloro-N-(2,6-dimethyl-1-piperidinyl)adenosine;

2-Chloro-N-(1-piperidinyl)adenosine;

2-Fluoro-N-(1-piperidinyl)adenosine;

2-Bromo-N-(1-piperidinyl)adenosine;

2-Chloro-N-(4-phenyl-1-piperidinyl)adenosine;

2-Chloro-N-(3-phenoxy-1-piperidinyl)adenosine;

2-Chloro-N-(4-phenoxy-1-piperidinyl)adenosine;

2-Chloro-N-(3-phenylthio-1-piperidinyl)adenosine;

2-Chloro-N-(4-phenylthio-1-piperidinyl)adenosine;

2-Chloro-N-(3-hydroxypiperidinyl)adenosine;

2-Chloro-N-(4-phenylsulphonyl-1-piperidinyl)adenosine; and pharmaceutically acceptable salts thereof.

7. The method according to claim 3, wherein the compound is selected from the group consisting of 2-Chloro-N-(2-phenyl-1-piperidinyl)adenosine;

N-(1-Piperidinyl)-2-(1-propoxy)adenosine;

2-Chloro-N-[2-(phenylthiomethyl)-1-piperidinyl]adenosine;

2-Methylthio-N-(1-piperidinyl)adenosine; and pharmaceutically acceptable salts thereof.

8. A method of treating myocardial or cerebral ischemia, comprising administering to a person in need thereof an effective amount of a compound of formula I:

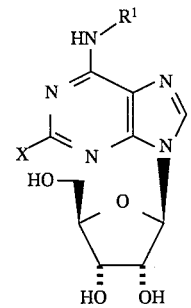

wherein

X is halogen, perhalomethyl, cyano, $C_{1-6}$-alkoxy, $C_{1-6}$-alkylthio or $C_{1-6}$-alkylamino;

$R^1$ is

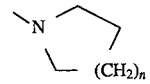

which is optionally substituted with one or two $C_{1-6}$-alkyl groups, $C_{2-6}$-alkenyl, $C_{2-6}$-alkynyl, phenoxy, phenylsulphonyl, phenylthio, hydroxy, phenyl, $C_{1-6}$-alkoxy or -$C_{1-6}$-alkyl-$C_{1-6}$-alkoxy, wherein n is 3; or a pharmaceutically acceptable salt thereof.

9. The method according to claim 8, wherein the compound is

2-Chloro-N-[1-(2,3,4,5,6,7-hexahydro)azepinyl]adenosine or a pharmaceutically acceptable salt thereof.

10. A method of treating myocardial or cerebral ischemia, comprising administering to a person in need thereof an effective amount of a compound of formula I:

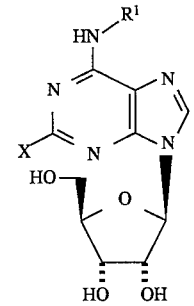

wherein

X is halogen, perhalomethyl, cyano, $C_{1-6}$-alkoxy, $C_{1-6}$-alkylthio or $C_{1-6}$-alkylamino;

$R^1$ is

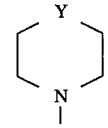

which is optionally substituted with $C_{1-6}$-alkyl, $C_{2-6}$-alkenyl, $C_{2-6}$-alkynyl, phenoxy, phenyl, $C_{1-6}$-alkoxy or -$C_{1-6}$-alkyl-$C_{1-6}$-alkoxy, wherein Y is O; or a pharmaceutically acceptable salt thereof.

11. The method according to claim 10, wherein the compound is

2-Chloro-N-(4-morpholinyl)adenosine or a pharmaceutically acceptable salt thereof.

12. A method of treating myocardial or cerebral ischemia, comprising administering to a person in need thereof an effective amount of a compound of formula I:

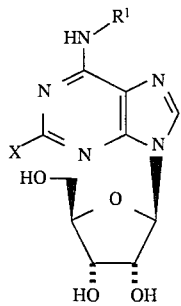

(I)

wherein

X is halogen, perhalomethyl, cyano, $C_{1-6}$-alkoxy, $C_{1-6}$-alkylthio or $C_{1-6}$-alkylamino;

$R^1$ is

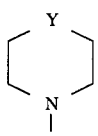

which is optionally substituted with $C_{1-6}$-alkyl, $C_{2-6}$-alkenyl, $C_{2-6}$-alkynyl, phenoxy, phenyl, $C_{1-6}$-alkoxy or -$C_{1-6}$-alkyl-$C_{1-6}$-alkoxy, wherein Y is S; or a pharmaceutically acceptable salt thereof.

13. A method of treating myocardial or cerebral ischemia, comprising administering to a person in need thereof an effective amount of a compound of formula I:

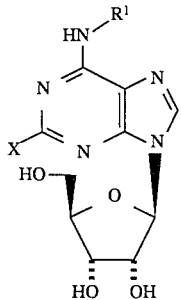

(I)

wherein

X is halogen, perhalomethyl, cyano, $C_{1-6}$-alkoxy, $C_{1-6}$-alkylthio or $C_{1-6}$-alkylamino;

$R^1$ is

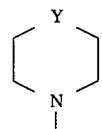

which is optionally substituted with $C_{1-6}$-alkyl, $C_{2-6}$-alkenyl, $C_{2-6}$-alkynyl, phenoxy, phenyl, $C_{1-6}$-alkoxy or -$C_{1-6}$-alkyl-$C_{1-6}$-alkoxy, wherein Y is NZ wherein Z is H, $C_{1-6}$-alkyl or phenyl; or a pharmaceutically acceptable salt thereof.

14. The method according to claim 13, wherein the compound is selected from the group consisting of 2-Chloro-N-(4-methyl-1-piperazinyl)adenosine;

2-Chloro-N-(4-phenyl-1-piperazinyl)adenosine; and pharmaceutically acceptable salts thereof.

15. A method of treating myocardial or cerebral ischemia, comprising administering to a person in need thereof an effective amount of a compound of formula I:

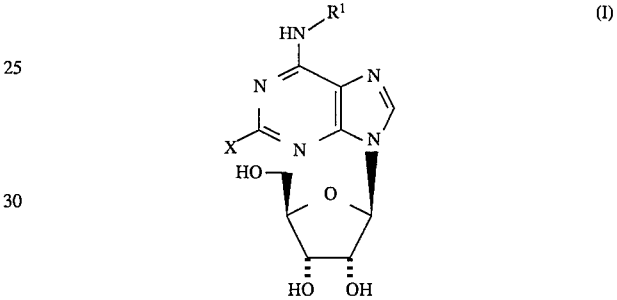

(I)

wherein

X is halogen, perhalomethyl, cyano, $C_{1-6}$-alkoxy, $C_{1-6}$-alkylthio or $C_{1-6}$-alkylamino;

$R^1$ is

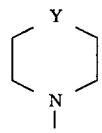

which is optionally substituted with $C_{1-6}$-alkyl, $C_{2-6}$-alkenyl, $C_{2-6}$-alkynyl, phenoxy, phenylthio, phenyl, $C_{1-6}$-alkoxy or -$C_{1-6}$-alkyl-$C_{1-6}$-alkoxy; or pharmaceutically acceptable salt thereof.

16. The method according to claim 15, wherein the compound is

2-Chloro-N-(4-phenyl-1,2,3,6-tetrahydro-1-pyridinyl)adenosine or a pharmaceutically acceptable salt thereof.

* * * * *